United States Patent [19]

Scudder, III

[11] 4,079,417
[45] Mar. 14, 1978

[54] DIGITAL VIDEO WINDOW CONTROL

[75] Inventor: Henry J. Scudder, III, Scotia, N.Y.

[73] Assignee: General Electric Company, Schenectady, N.Y.

[21] Appl. No.: 703,096

[22] Filed: Jul. 6, 1976

[51] Int. Cl.² .............................................. H04N 5/14
[52] U.S. Cl. ................................... 358/111; 358/166; 358/180
[58] Field of Search ................ 358/111, 180, 166, 160

[56] References Cited
U.S. PATENT DOCUMENTS

| | | | |
|---|---|---|---|
| 3,920,889 | 11/1975 | Connor | 358/166 |
| 3,969,571 | 7/1976 | Fenyo | 358/166 |

OTHER PUBLICATIONS

H. G. Andrew, Image Processing by Digital Computer, I.E.E.E. Spectrum 7-72, pp. 20-32.
Y. M. Ting, Fingerprint Image Enchancement System, I.B.M. Technical Disclosure Bulletin, vol. 16, No. 8, 1-74.

Primary Examiner—Robert L. Griffin
Assistant Examiner—Edward L. Coles
Attorney, Agent, or Firm—Lawrence D. Cutter; Joseph T. Cohen; Jerome C. Squillaro

[57] ABSTRACT

A digital signal processor is connected between a refresh memory at the output of the digital computer in an x-ray tomography system and the digital-to-analog converter of a cathode ray tube display to provide a limited resolution gray scale display of a selected portion from an image signal having wide dynamic range.

11 Claims, 2 Drawing Figures

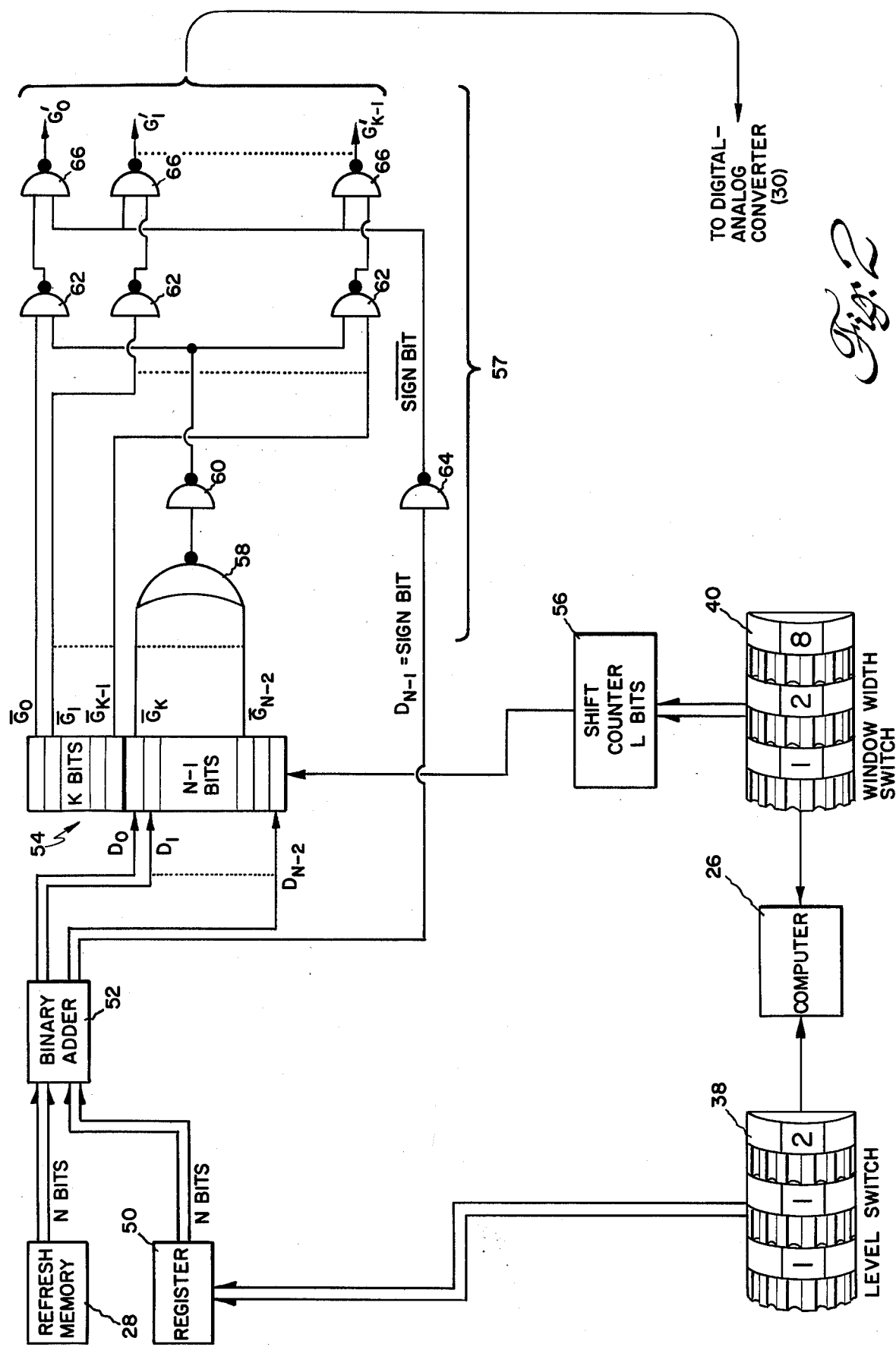

DIGITAL VIDEO WINDOW CONTROL

BACKGROUND OF THE INVENTION

This invention relates to the display of digital data. More specifically, this invention related to apparatus for increasing the available dynamic range in a cathode ray tube display of x-ray tomographic images.

Photographic displays of x-ray absorption characteristics have, for over half a century, been a principal tool for medical diagnosis. Variations in the density of a silver image on a photographic transparency are utilized to represent the x-ray absorption characteristics of internal body tissues. Conventional x-ray photorgraphy is, however, limited to the display of superimposed shadows of bodily organs lying in a transmission path. The characteristics of silver halide photographic emulsions tend to limit the x-ray absorption density resolution of images so displayed.

More recently, a method of x-ray tomography has been utilized to provide high resolution, sectional displays of internal tissue structures. In accordance with this method, x-ray transmission characteristics are measured along a plurality of paths through an object undergoing examination. Images of x-ray absorption densities within the object are then constructed by computations on the x-ray transmission data. The calculations are most advantageously performed in a digital computer and the images may be displayed, for example, on a cathode ray tube. A specific method of x-ray tomographic imaging is, for example, described in U.S. Pat. No. 3,778,614 to Hounsfield, which is incorporated by reference, as background material in this disclosure.

X-ray tomographic methods are capable of producing images having far greater absorption density resolution than images produced by photographic techniques. For example, present tomographic image reconstruction methods are capable of quantitizing x-ray absorbtion density measurements into 256 or more separate levels. Cathode ray tube (CRT) data displays are incapable, however, of displaying more than approximately 15 distinct gray-scale levels.

Significant medical information, for example, the presence of tumors in soft tissue, is often represented by minimal level changes in tomographic image density. The detection of such level changes is often accomplished by a process wherein a radiologist views a computer-generated CRT image having a limited gray-scale range and, on the basis of his observation and experience, interactively modifies the computer program to present the most significant density information within the dynamic range of the CRT display. The observations and procedures inherent in this process are, of course, highly subjective so that a lengthy series of iterations may be required to obtain an optimum display. Each modification to the computer program will, in general, cause an interruption in the processing of other tomographic image information and, by distracting the radiologist's attention from the display screen will lengthen the image interpretation process.

A copending U.S. patent application Ser. No. 618,862, filed Oct. 1, 1975 by George W. Ellis, which is assigned to the assignee of this invention, describes an analog signal processor which allows interactive modification of a CRT display of tomographic information. That disclosure is incorporated by reference herein as background material.

SUMMARY OF THE INVENTION

In accordance with the present invention, I provide a digital processor unit for connection between the ouput of a digital computer and the video input of a cathode ray tube display. The digital processor allows display of an analog signal having a limited dynamic resolution which may be selected from within a signal having wide dynamic range. A radiologist may, by use of the processor, interactively select and modify the level and dynamic range of a cathode ray tube display to most advantageously view high resolution data. The processor operates upon digital output data and may, therefore, accomplish highly accurate modification of a displayed image without program changes or additional computer processing time.

It is, therefore, an object of this invention to provide interactive means for adjusting the level and dynamic range of a cathode ray tube display.

It is another object of this invention to reduce the central computer processor time required for the display and interpretation of tomographic x-ray images.

BRIEF DESCRIPTION OF THE DRAWINGS

The novel features believed characteristic of the present invention are set forth in the appended claims. The invention itself, together with further objects and advantages thereof, may be best understood with reference to the following detailed description, taken in connection with the appended drawings in which:

FIG. 2 is a simplified schematic diagram of the digital processor of the present invention.

DESCRIPTION OF THE PREFERRED EMBODIMENT

Figure 1:
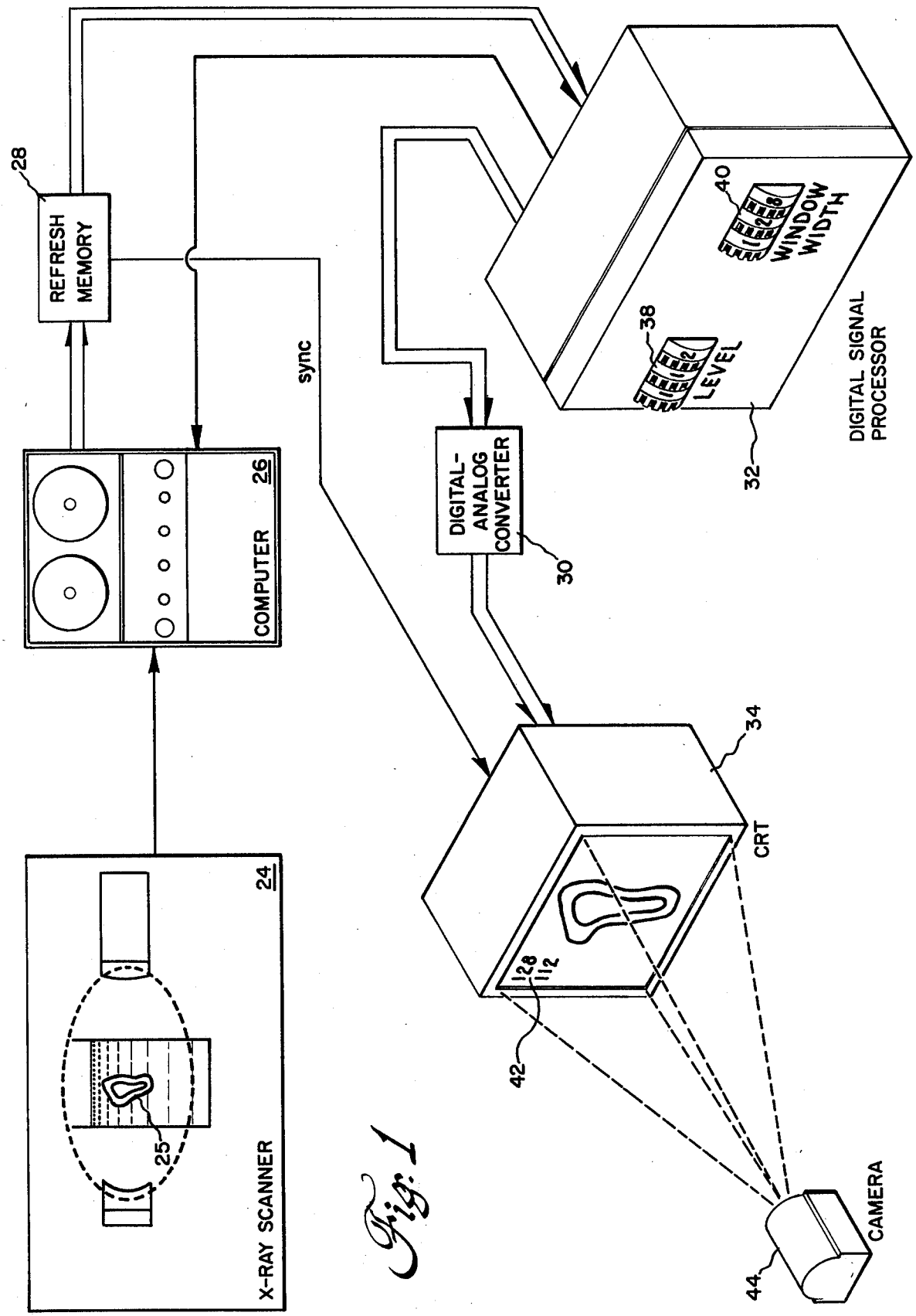
FIG. 1 is a tomographic imaging system incorporating the processor of the present invention.

Tomographic x-ray image information is generally generated from x-ray detector signals by the solution of large numbers of simultaneous equations in a digital computer. The output signal of the computer represents a matrix wherein each element is a numerical value of the x-ray absorption density over a particular discrete area (pixel) in an image plane. X-ray tomographic systems are capable of resolving small differences of x-ray absorption density and are therefore extremely useful, for example, in the detection of soft tissue tumors. The x-ray absorption density resolution of a given system is a function of the x-ray dosage administered to a patient and the computation time utilized for construction of the image. Present tomographic measurement systems typically resolve 256 or more discrete levels of x-ray absorption density.

The image matrix signal generated by the computer is most advantageously stored, in digital form, in a refresh-buffer memory, the contents of which are serially scanned and converted into analog form for presentation to the intensity modulation input of a cathode ray tube. Such an analog signal generally carries far more density information than may be displayed on a cathode ray tube which may, for example, be limited to resolving approximately 15 distinct intensity levels. It has been found, however, that significant medical information is often represented by minimal changes within a signal having a large dynamic range.

In accordance with the present invention, I provide a digital processor wherein a small portion, or window, extracted from within the larger dynamic range of a signal may be expanded to fill the gray-scale of a cathode ray tube. The level and width of the window with relation to the overall signal envelope may be adjusted to provide an optimum cathode ray tube display.

FIG. 1 schematically illustrates a typical x-ray tomography system incorporating the present invention. An x-ray scanner 24 produces electrical output signals corresponding to the x-ray absorption characteristics along a plurality of transmission paths through an object 25. The output signals from scanner 24 are applied at the inputs of a digital computer 26 wherein well-known computational algorithms are applied to produce digital matrix signals corresponding to a sectional image of x-ray absorption densities within the object 25. The digital matrix signals are transmitted from the computer 26 to a refresh memory 28 where they are stored for transmission to a display. The contents of the refresh memory 28 are sequentially scanned into a digital signal processor 32 (more fully described below) which selectively expands portions of the signal to match the gray-scale range of a cathode ray tube display. The expanded signal produced by the digital signal processor 32 is applied to digital-analog converter 30 which transforms it into an analog output signal wherein voltage levels correspond to intensity levels in a raster scanned display of the image. The output of the digital-analog converter 30 is applied to the intensity modulation input of a cathode ray tube display 34 in conjunction with raster synchronization signals which are generated within the refresh memory 28 in a conventional manner.

The digital signal processor 32 is equipped with a LEVEL control 38 which permits the operator to adjust the value of a voltage level in the analog signal corresponding to the base level (lowest gray level) presented on the display 34. The window width (range of the signal levels presented on the gray scale of the display 34) is likewise adjustable, in steps equal to the powers of 2, by means of a WINDOW WIDTH control 40 at the digital signal processor 32.

Under the control of the digital computer 26, x-ray image information is transferred to the refresh memory 28 and presented on the cathode ray tube display 34. A radiologist or tomograph operator manipulates the controls of the digital signal processor 32 to most advantageously display medically significant information on the cathode ray tube screen.

FIG. 2 is a simplified schematic diagram of the digital signal processor 32. The high resolution digital output of the refresh memory 28, comprising words of N data bits, each is applied to one input of a binary adder 52. The output of the LEVEL switch 38, an N bit number representing the darkest gray level of the display, is stored in a register 50. The two's complement of the LEVEL switch 38 output is applied from the register 50 to a second input of the binary adder 52. Thus, the output of the binary adder 52 is the two's complement difference of the LEVEL switch output subtracted from the output of the refresh memory 28. The lowest order N-1 bits from the output of the binary adder 52 are stored in the N-1 highest order positions of a shift register 54. The shift register 54 comprises a total of K + N-1 bit positions where N is the binary resolution of the digital output from the refresh memory 28 and K is the binary gray scale resolution of the CRT display 34 (FIG. 1).

The output of the WINDOW WIDTH switch 20, which is a binary number representing a range enhancement factor and is an even power of 2, is stored in shift counter 56 and is applied as a shift control to the shift register 54. The base level stored in register 50 is subtracted from the image signal in the binary adder 52 and the difference stored in the high order positions of the shift register 54. The contents of the register 54 are then shifted $L = \log_2 R$ bits to the right to accomplish the gray scale range compression. A graphical output G is then taken from the low order K bits of the shift register.

In the event that the graphical output lies outside the range of the cathode ray tube display, a logic network 57 determines the value of the signal G' which is supplied to the digital-to-analog converter. If the graphical output exceeds the range of the display window, one or more of the high order shift register bits $G_K$ through $G_{N-2}$ will have a non-zero value. These outputs of the shift register are combined in a NOR gate 58 and an inverter 60, the output of which is NANDed in gates 62 with the graphic output bits $G_O$ through $G_{K-1}$. If the graphical output is less than the base level, the sign bit $D_{N-1}$ produced by the binary adder 52 will be non-zero. The outputs of the NAND gates 62 are again NANDed in gates 66 with the inverted output of the binary adder 52 sign bit. The output of the logic network 57, which is applied to the digital-to-analog converter 30 may, thus, be described by the equations:

$G' = 0$ if $D = X - M$ is negative;
$G' = 2^K - 1$ if $D > R = 2^L \rightarrow x > M + R$; and
$G' = D/2^{L-K}$ otherwise;

where R is the window width = $2^L$.

The output of the LEVEL switch 38 and of the WINDOW WIDTH switch 40 may, if desired, be transmitted to the computer and incorporated into the image display as numerical information 42 (FIG. 1).

It may be desirable, in some situations, to control the display of the base level and window width by means of a stored program in the computer 26. In such cases the LEVEL switch 38 and the WINDOW WIDTH switch 40 may be replaced by registers which are driven from digital signals generated within the computer 26.

The digital processor unit may be installed adjacent the cathode ray tube display to permit rapid adjustment by a radiologist whose attention may be continuously directed to the displayed image. The signal processor operates on a digital signal generated from a refresh memory to modify a displayed image on a cathode ray tube display and, therefore, is highly stable and does not require computer processor time or interruption and modification of the precursor computer program to effect display modification.

While the invention has been described in detail herein in accordance with the preferred embodiment thereof, many modifications and changes therein may be effected by those skilled in the art. Accordingly, it is intended by the appended claims to cover all such modifications and changes as fall within the true spirit and scope of this invention.

The invention claimed is:

1. In an X-ray tomographic imaging system of the type comprising:
    a source of radiation transmission data, a digital computer connected to receive said transmission data and to calculate therefrom high resolution digital tomographic image data, a digital-to-analog converter connected to receive digital image data and to produce therefrom an analog image waveform, and an image display connected to receive and present the analog image waveform in an intensity modulated, visual format; the improvement comprising:

a digital data processor connected to receive the high resolution digital image data and to convert that data into a limited resolution signal at an input of the digital-to-analog converter, the limited resolution signal, G', comprising an expanded function of values of the high resolution signals, G, falling within the range of a selectable window function with upper and lower levels, said combined expanding and window functions relation G and G' as follows:

if G is below the lower window level, then G' equals the lowest intensity value and if G is above the upper window level, then G' is equal to the highest window value, and if G is between the window levels, then G' is proportional to $2^K$, said proportion being between 0 and 1 being determined by the position of G wihthin the window, where K is the resolution, in bits, of the image display, whereby the intensity resolution of the image display is selectively increased.

2. The imaging system of claim 1 wherein the digital data processor comprises means for subtracting a reference digital signal from the high resolution data signal.

3. The imaging system of claim 2 wherein the means for subtracting comprises a binary adder connected to receive the high resolution digital data signal and the two's complement of the reference digital signal.

4. The imaging system of claim 2 wherein the digital data processor further comprises means for dividing the difference of the high resolution data signal and the reference digital signal by a scale factor.

5. The imaging system of claim 4 wherein the scale factor is an even power of 2.

6. The imaging system of claim 4 wherein the means for dividing comprises a shift register.

7. The imaging system of claim 6 wherein the high resolution digital data signal has an accuracy of N bits, the reference signal has an accuracy of N bits, the image display has a resolution of K bits, and wherein the shift register consists of $N + K - 1$ bits positions.

8. The imaging system of claim 7 wherein said digital analog converter is a K bit digital-to-analog converter.

9. The imaging system of claim 8 wherein the output of the adder is applied to the N most significant bit positions of the shift register and wherein the output of the shift register is taken from the K least significant bit positions of the shift register.

10. The imaging system of claim 7 further comprising a logic network connected to receive the output of the shift register and a sign bit output of the binary adder and to produce therefrom the limited resolution signal, G', in accordance with the equations:

$G' = 0$ if $D$ is negative;
$G' = 2^K - 1$ if $D > R$; and
$G' = D/2^{L-K}$ otherwise, where $D$ is the output of the shift register and $R = 2^L$ is the scale factor.

11. A digital signal processor for connection between a high resolution digital signal source and a limited resolution digital display comprising:

digital subtracting means connected to receive a high resolution digital data signal and a digital reference signal and for producing therefrom an output signal, D, representative of the difference of said reference signal subtracted from said video signal;

a shift register connected to receive the output of said subtracting means and to selectively divide said output of said subtracting means by R, and even power of 2; and logic means connected to receive the output of said shift register and said subtracting means and to produce therefrom an output signal, G', in accordance with the equations:

$G' = 0$ if D is negative;
$G' = 2^K - 1$ if $D > R$; and
$G' = D/2^{L-K}$ otherwise;

where $L = \log_2 R$.

* * * * *